(12) United States Patent
In et al.

(10) Patent No.: US 11,280,697 B2
(45) Date of Patent: Mar. 22, 2022

(54) DYNAMIC CHARACTERISTIC MEASUREMENT DEVICE

(71) Applicant: Saginomiya Seisakusho, Inc., Tokyo (JP)

(72) Inventors: Eisei In, Sayama (JP); Kohei Hizono, Sayama (JP)

(73) Assignee: Saginomiya Seisakusho, Inc., Tokyo (JP)

( * ) Notice: Subject to any disclaimer, the term of this patent is extended or adjusted under 35 U.S.C. 154(b) by 0 days.

(21) Appl. No.: 17/295,215

(22) PCT Filed: Sep. 12, 2019

(86) PCT No.: PCT/JP2019/035957
§ 371 (c)(1),
(2) Date: May 19, 2021

(87) PCT Pub. No.: WO2020/105251
PCT Pub. Date: May 28, 2020

(65) Prior Publication Data
US 2021/0389208 A1 Dec. 16, 2021

(30) Foreign Application Priority Data
Nov. 19, 2018 (JP) .............................. JP2018-216485

(51) Int. Cl.
*G01M 7/02* (2006.01)
*G01N 3/38* (2006.01)

(52) U.S. Cl.
CPC ............ *G01M 7/022* (2013.01); *G01M 7/025* (2013.01); *G01N 3/38* (2013.01)

(58) Field of Classification Search
CPC .... G01N 3/32; G01N 3/38; G01N 2203/0005; G01N 2203/0008; G01N 2203/0051; G01M 7/00; G01M 7/022; G01M 7/025
See application file for complete search history.

(56) References Cited

U.S. PATENT DOCUMENTS

| 4,445,381 A | * | 5/1984 | Russenberger | .......... | G01N 3/38 |
| | | | | | 73/666 |
| 4,916,391 A | * | 4/1990 | Doerman | ................ | G01G 9/00 |
| | | | | | 177/1 |

(Continued)

FOREIGN PATENT DOCUMENTS

| JP | S61-022251 B2 | 5/1986 |
| JP | S64-013434 A | 1/1989 |

(Continued)

OTHER PUBLICATIONS

Korean Office Action, English translation, from KR10-2021-7014837, filed May 17, 2021, dated Jul. 1, 2021.

*Primary Examiner* — Natalie Huls

(74) *Attorney, Agent, or Firm* — Workman Nydegger

(57) ABSTRACT

An object of the present invention is to provide a dynamic characteristic measurement device capable of accurately measuring dynamic vibration characteristics of a rubber isolator and the like in a high-frequency vibration range. A dynamic characteristic measurement device according to the present invention includes a base, a support part that is placed above the base so as to be capable of floating via an air spring, an electrodynamic vibrator that is provided on the base side of an object under test mounted between the base and the support part and vibrates the object under test, and a load washer that is provided on the support part side of the object under test and measures a dynamic load applied to the object under test. Here, a crosshead of the support part is shaped such that a resonant frequency is at least 3 kHz.

8 Claims, 7 Drawing Sheets

(56) References Cited

U.S. PATENT DOCUMENTS

| | | | | |
|---|---|---|---|---|
| 6,023,980 A * | 2/2000 | Owen | ............ | G01N 3/38 73/797 |
| 6,813,960 B1 * | 11/2004 | Owen | ............ | G01N 3/32 73/794 |
| 9,442,053 B2 * | 9/2016 | Melz | ............ | G01N 3/32 |
| 2012/0318065 A1 * | 12/2012 | Neviere | ............ | G01N 3/32 73/649 |
| 2013/0104662 A1 * | 5/2013 | Rogers | ............ | G01M 7/022 73/663 |
| 2015/0219539 A1 * | 8/2015 | Mary | ............ | G01M 5/0075 73/799 |
| 2015/0268127 A1 * | 9/2015 | Berchtold | ............ | G01M 7/02 73/662 |
| 2016/0341629 A1 * | 11/2016 | Schaefer | ............ | G01M 7/025 |

FOREIGN PATENT DOCUMENTS

| | | |
|---|---|---|
| JP | 2004219196 A | 8/2004 |
| JP | 2004-347441 A | 12/2004 |
| JP | 2007-113944 A | 5/2007 |
| JP | 2007-271268 A | 10/2007 |
| JP | 2016-218080 A | 12/2016 |
| WO | 2009/130818 A1 | 10/2009 |

\* cited by examiner

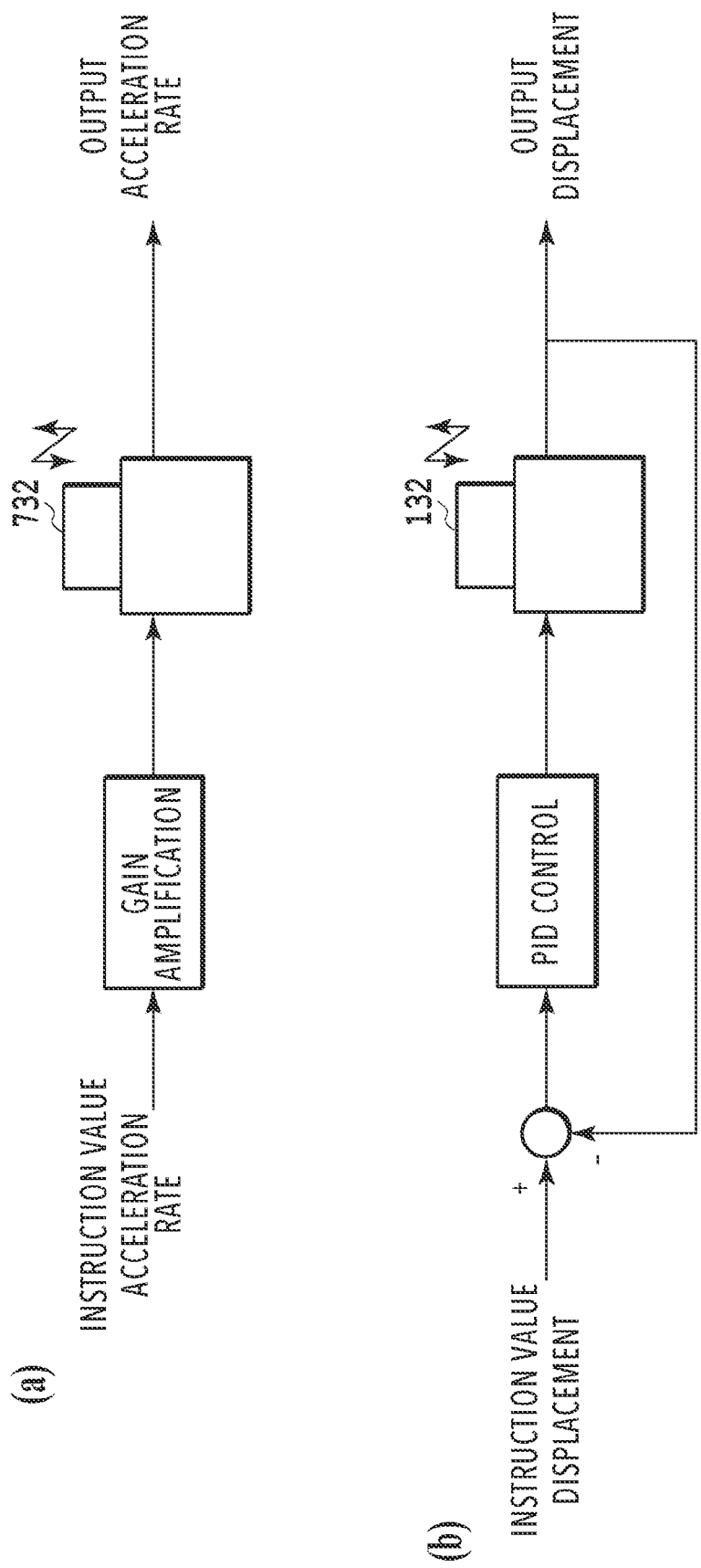

DYNAMIC CHARACTERISTIC MEASUREMENT DEVICE

TECHNICAL FIELD

The present invention relates to a dynamic characteristic measurement device, or more specifically, to a dynamic characteristic measurement device to measure dynamic characteristics of a rubber isolator for an automobile and the like.

BACKGROUND ART

Dynamic characteristics of a rubber isolator are key factors for determining vibration isolation, ride comfort, steering stability, kinematic performances, sound isolation, and energy saving performances of an automobile and the like. Control of the dynamic characteristics is an important issue not only for rubber isolator manufacturers but also for automobile manufacturers. The dynamic performances of the rubber isolators are influenced by frequencies, environmental temperatures, amplitudes, preloads, and the like. Accordingly, advanced design techniques, measurement techniques, and signal processing techniques are essential for achieving measurements at high accuracy.

As for dynamic properties of rubber isolators, there have been strong demands for improvements in dynamic properties of products and enhancement in management levels with a central focus mainly on rubber isolators for automobiles. Accordingly, testing methods have been standardized as defined in SRIS 3503 (The Society of Rubber Science and Technology, Japan Standards), for example. Note that the dynamic properties referred to herein are collective terms including a storage spring constant, a loss spring constant, an absolute spring constant, an attenuation coefficient, a loss coefficient, and a phase angle.

PTL 1 describes a dynamic characteristic testing device configured to install a vibrator, a test piece, and a load detector in series between a base member and a support member, which is placed on the base member via an elastic body, in such a way as to apply a dynamic load from the vibrator to the test piece, and to set a mass on the support member side and a spring constant of the elastic body such that a resonance frequency to be determined by the mass on the support member side supported by the base member via the elastic body and the spring constant of the elastic body becomes sufficiently smaller than a vibration frequency by the vibrator.

Meanwhile, PTL 2 describes a dynamic characteristic measurement device for a rubber isolator, which is a measurement device configured to perform a dynamic characteristic measurement by using a load cell while repeatedly applying loads to a test piece such as a rubber isolator, which adopts a piezoelectric element type load cell prepared by arranging three or more piezoelectric elements in parallel as the load cell.

In the meantime, PTL 3 describes a dynamic characteristic measurement device in which a rubber isolator is sandwiched in a direction of vibration between a first support member and a second support member that are fixed to a base via an elastic body, and the first support body is disposed on an opposite side of a vibration side and has a sufficient mass for not being influenced by the vibration. Here, a pressing device applies a constant load from outside of the elastic body to the rubber isolator via the elastic body in a direction that one of the first support member and the second member approaches the other one of the first support member and the second member, and the rubber isolator is vibrated by a vibrator from outside.

On the other hand, hybrid type vehicles and electric vehicles which utilize rotatory power of electric motors have been rapidly diffused in recent years in addition to conventional vehicles that utilize gasoline engines. A vibration range of such an electric motor exceeds a vibration range of a conventional reciprocating engine around 1.5 kHz and reaches a high-frequency range up to 5 kHz. Particularly, in order to analyze factors including noise, vibration, harshness (NVH), and the like which disturb drivers and passengers, there is a growing need for measuring dynamic vibration characteristic data in a high-frequency range up to 3 kHz regarding a rubber isolator used in a vehicle that mounts the aforementioned electric motor.

CITATION LIST

Patent Literature

PTL 1: Japanese Patent Publication No. 61-22251
PTL 2: Japanese Patent Laid-Open No. 64-13434
PTL 3: Japanese Patent Laid-Open No. 2007-271268

SUMMARY OF INVENTION

Technical Problems

However, the conventional dynamic characteristic measurement apparatus as described in PTL 1 or 2 has the upper limit of the vibration frequency of about 1.5 kHz due to its structure, and cannot therefore deal with the vibration in the aforementioned high-frequency range.

In the meantime, although PTL 3 describes the dynamic characteristic measurement device that embeds the vibrator capable of applying the vibration up to about 5 kHz and the mechanism for applying the constant load by using the pressing device in order to deal with the high frequency. However, PTL 3 does not include a description as to whether or not the device can perform an accurate measurement up to a high frequency.

In other words, the measurement of the dynamic characteristics in the high-frequency vibration range has a problem that it is difficult to perform an accurate measurement in a range around the resonance frequency unless a resonance point of a frame is set higher than a range of the measurement frequency. Meanwhile, particularly in the case of a rubber isolator for an automobile and the like, it is necessary to measure the dynamic characteristics in a state of application of a high load (a preload) on the assumption of a state of an actual vehicle. However, in the state of applying the preload as mentioned above, it is necessary to broaden a measurement range in a measurement with a load detector. Hence, there is a problem of a difficulty in measuring a small dynamic load at a high frequency. On the other hand, while a high vibration capacity and a high amplitude which are proportional to a square of the frequency are required in the high-frequency vibration range, a resonance frequency drops in a case where a weight is reduced in order to activate an electrodynamic vibrator at a high speed. This drop in vibration capacity also leads to a problem of a difficulty in obtaining a required vibration amplitude.

Accordingly, it is an object of the present invention to provide a dynamic characteristic measurement device, which is capable of measuring a small dynamic load in a state of applying a preload while eliminating an influence of a resonance frequency of a frame even in a high-frequency vibration range up to 3 kHz, and of accurately measuring dynamic vibration characteristics of a rubber isolator and the like in the high-frequency vibration range by increasing a level of vibration of an object under test.

Solution to Problem

To solve the aforementioned problems, a dynamic characteristic measurement device of the present invention provides a dynamic characteristic measurement device including: a base; a support part that is placed above the base so as to be capable of floating via an elastic body; an electrodynamic vibrator provided on the base side of an object under test mounted between the base and the support part and configured to vibrate the object under test; and a dynamic load measuring instrument provided on the support part side of the object under test and configured to measure a dynamic load applied to the object under test. Here, the shape of support part is such that a resonant frequency is at least 3 kHz.

Meanwhile, the dynamic characteristic measurement device may further include a static load measuring instrument attached to the electrodynamic vibrator and configured to measure a static load applied to the object under test.

In the meantime, the static load measuring instrument may be attached to a resonant jig attached to the electrodynamic vibrator.

Meanwhile, an accelerometer configured to remove an influence of the dynamic load to the support part may be attached to the dynamic load measuring instrument.

In the meantime, a position sensor configured to measure a position of the electrodynamic vibrator may be attached to the electrodynamic vibrator, and displacement of the electrodynamic vibrator is controlled by feedback control based on a displacement signal from the position sensor.

Meanwhile, a preload may be applied from the electrodynamic vibrator side to the object under test.

Moreover, the preload may be applied together with the electrodynamic vibrator and air provided on the electrodynamic vibrator side.

Advantageous Effects of Invention

According to the present invention, it is possible to provide a dynamic characteristic measurement device, which is capable of measuring a small dynamic load in a state of applying a preload while eliminating an influence of a resonance frequency of a frame even in a high-frequency vibration range up to 3 kHz, and of accurately measuring dynamic vibration characteristics of a rubber isolator and the like in the high-frequency vibration range by increasing a level of vibration of an object under test.

BRIEF DESCRIPTION OF DRAWINGS

FIG. 7A is a block diagram illustrating open loop control of a conventional electrodynamic vibrator vibrating table and FIG. 7B is a block diagram illustrating closed loop feedback control of the electrodynamic vibrator vibrating table.

DESCRIPTION OF EMBODIMENT

An embodiment of the present invention will be described below with reference to the drawings.

Note that the concept of upper and lower positions in the following description corresponds to upper and lower positions in FIG. 2A, for example, which indicates a relative positional relation between respective components but does not indicate an absolute positional relation therebetween.

Figure 1:
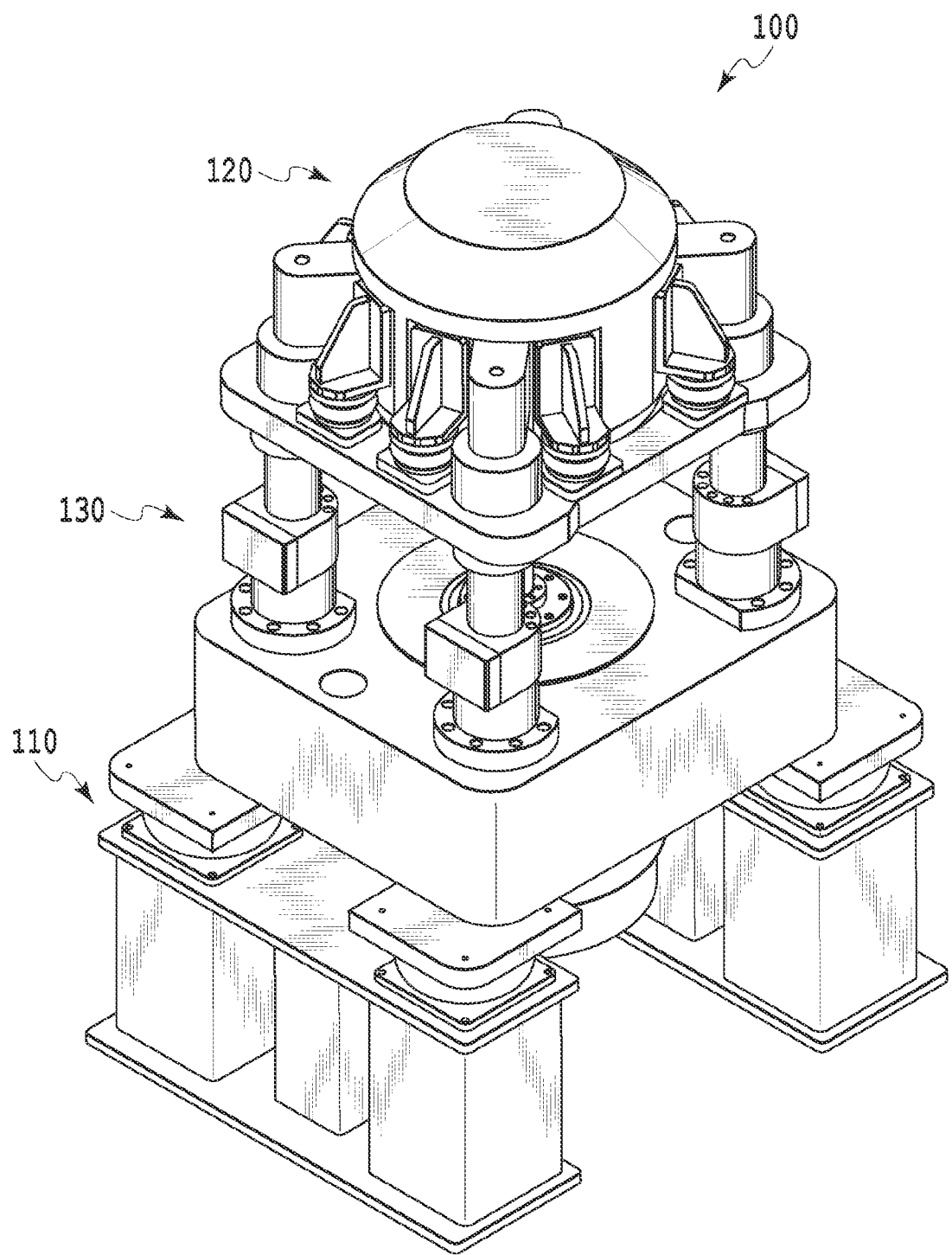
FIG. 1 is a perspective view illustrating an example of a dynamic characteristic measurement device according to the present invention.

FIG. 1 is a perspective view illustrating an exemplary dynamic characteristic measurement device 100 according to the present invention. FIG. 2A is a partial cross-sectional view illustrating the dynamic characteristic measurement device 100 shown in FIG. 1 and being viewed from a front face, and FIG. 2B is an enlarged cross-sectional view illustrating a portion IIb shown in FIG. 2A. FIG. 3 is a side view illustrating a state of stretching support pillars of the dynamic characteristic measurement device 100 shown in FIG. 2A.

Figure 2:
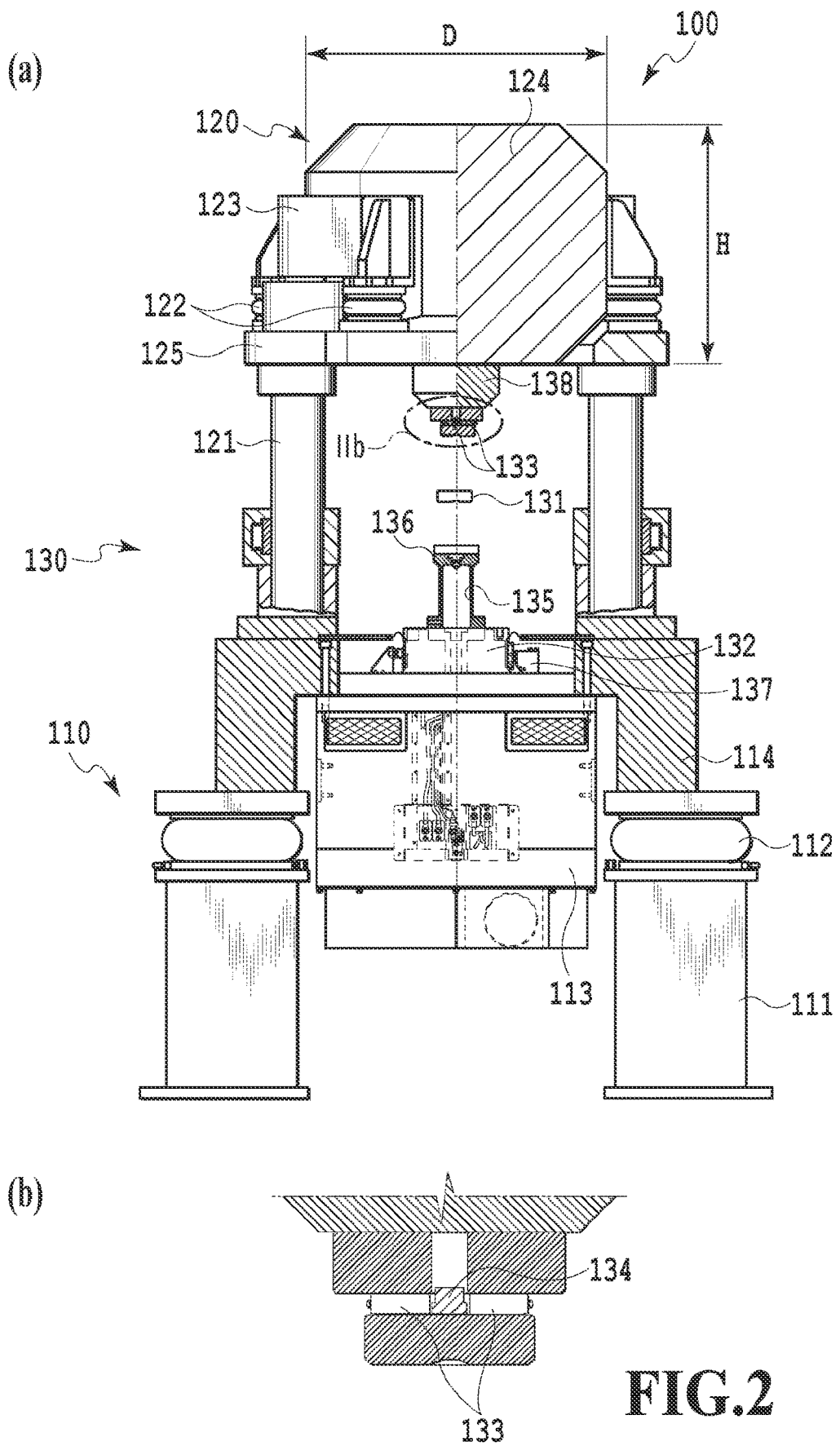
FIG. 2A is a partial cross-sectional view illustrating the dynamic characteristic measurement device shown in FIG. 1 and being viewed from a front face.
FIG. 2B is an enlarged cross-sectional view illustrating a portion IIb shown in FIG. 2A.
Figure 3:
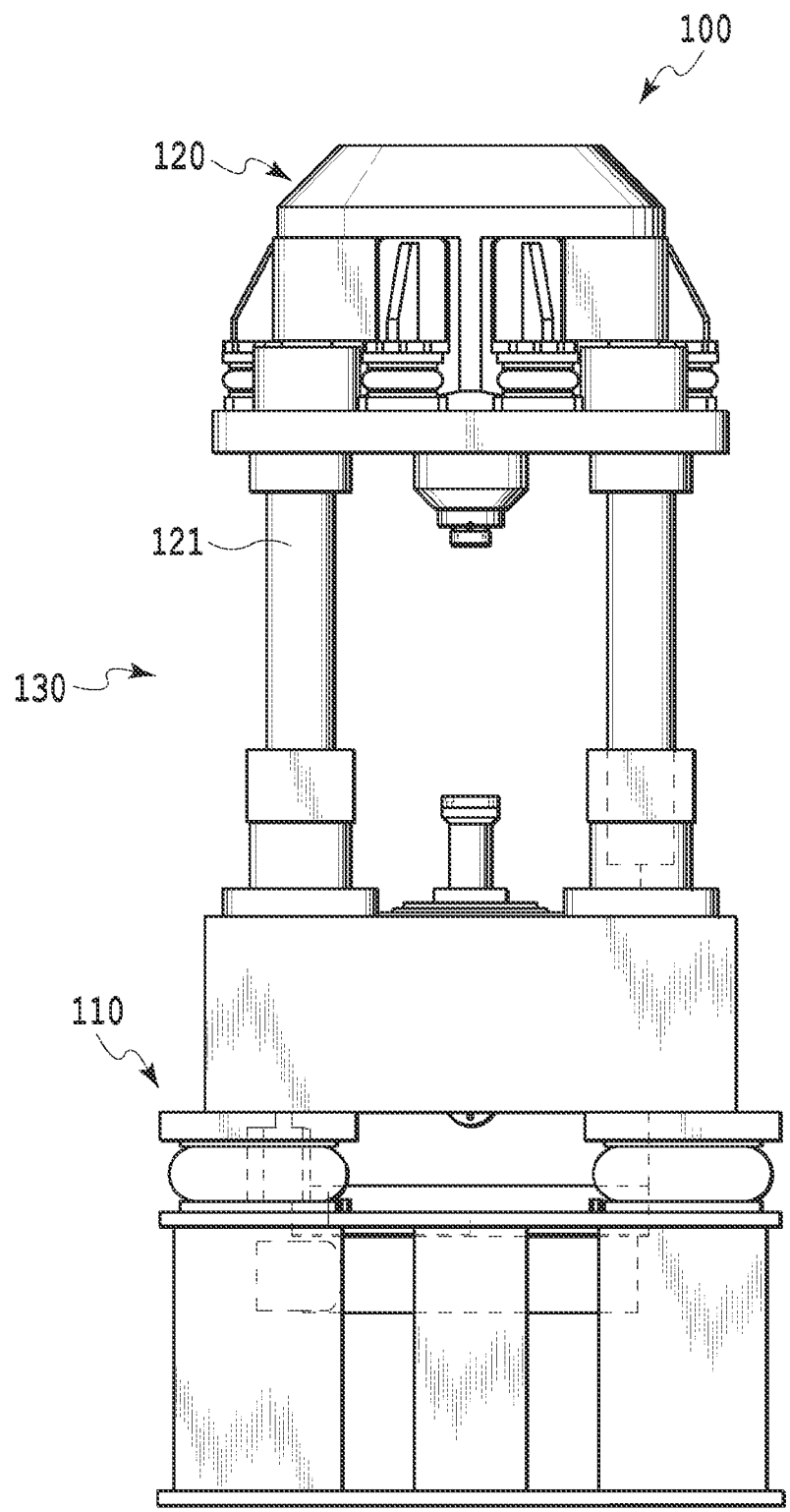
FIG. 3 is a side view illustrating a state of stretching support pillars of the dynamic characteristic measurement device shown in FIG. 2A.

In FIGS. 1 to 3, the dynamic characteristic measurement device 100 is a measurement device that measures dynamic properties of a rubber isolator for an automobile and the like, which are standardized as defined in SRIS 3503 (The Society of Rubber Science and Technology, Japan Standards), for example. Note that the dynamic properties referred to herein are collective terms including a storage spring constant, a loss spring constant, an absolute spring constant, an attenuation coefficient, a loss coefficient, and a phase angle.

The dynamic characteristic measurement device 100 includes a base 110, a support part 120 that is placed above the base 110 so as to be capable of floating via an elastic body such as an air spring 122 to be described later, and a measurement unit 130 arranged between the base 110 and the support part 120.

The base 110 includes leg parts 111, air springs 112, an electrodynamic vibrator 113, and a base mount part 114.

The leg parts 111 are arranged at positions located on a lower side illustrated in FIG. 2A and in contact with a ground, thus fixing the dynamic characteristic measurement device 100 to the ground. Here, the dynamic characteristic measurement device 100 is fixed to the ground by using four leg parts 111. However, such an attachment unit is not limited to this configuration as long as the attachment unit can endure outside factors such as earthquakes, because transmission of vibration is prevented by attachment to a body part via the air springs 112 as described below.

Here, four air springs 112 are provided, each of which is arranged between corresponding one of the four leg parts 111 and the body part of the dynamic characteristic measurement device 100. The four air springs 112 are provided in order to prevent transmission of vibration between the ground and the dynamic characteristic measurement device 100 in the course of a vibration test.

The electrodynamic vibrator 113 is attached to the base mount part 114 of the dynamic characteristic measurement device 100 and connected to a control system 200 to be described later so as to drive an electrodynamic vibrator vibrating table 132 to be described later. A set of the base mount part 114 and the electrodynamic vibrator 113 has a sufficient mass and plays a role for preventing vibration transmission in conjunction with the above-mentioned air springs 112.

The support part 120 includes support pillars 121, air springs 122, fasteners 123, a crosshead 124, and an intermediate plate 125.

Here, four support pillars 121 are arranged above the base 110 so that the crosshead 124 can be placed above, and are joined to the intermediate plate 125. Note that the support pillars 121 of the dynamic characteristic measurement device 100 can also be stretched as illustrated in FIG. 3. The stretchable support pillars 121 as mentioned above make it possible to house and measure a constant temperature bath into the measurement unit 130, and to measure an object 131 under test which is large in size.

Each air spring 122 is an elastic body that is placed above the intermediate plate 125. Provision of the air springs 122 makes it possible to establish a floating state of blocking transmission of vibration such as resonance between the crosshead 124 placed above the air springs 122 and the base 110 in a state of high-frequency vibration and the like. Although the dynamic characteristic measurement device 100 is provided with eight air springs 122 as illustrated in FIG. 1, the present invention is not limited to this configuration. A different quantity of the air springs 122 may be provided as long as the floating state can be established therewith.

The fasteners 123 are driven by a hydraulic pressure, an air pressure, or the like. The fasteners 123 are provided in order to fix the crosshead 124 to the intermediate plate 125 and to release the floating state. Here, the case of releasing the floating state may conceivably involve a case in which the base mount part 114, the support pillars 121, the intermediate plate 125, and the crosshead 124 are rigidly joined to one another to have high rigidity, and the object under test is subjected to a measurement of its static spring constant, a measurement at a low vibration frequency such as a frequency in a range from about 100 to 150 Hz inclusive, and so forth. Meanwhile, the fasteners 123 are installed at four positions in this case as illustrated in FIG. 1. However, the number of the fasteners 123 installed is not limited to this number as long as sufficient coupling rigidity is available.

The crosshead 124 is placed above the base 110 so as to be capable of floating via the air springs 122. A vibration range of electric motors for hybrid-type vehicles and electric vehicles reaches a high-frequency range in excess of 1.5 kHz that represents a vibration range of conventional reciprocating engines. Here, a measurement takes place in a high-frequency vibration range up to 3 kHz. In this case, if a resonance frequency unique to the crosshead 124 is low, the crosshead 124 may be resonated during the measurement whereby an accurate measurement is infeasible. Accordingly, the resonance frequency of the crosshead 124 needs to be set to a higher frequency than a measurement range to be examined.

In the dynamic characteristic measurement device 100 of the present invention, the crosshead 124 is formed into such a shape that has a sufficient weight (1500 kg or above) so as to raise the resonance frequency of the cross head 124. Moreover, this shape is formed into a shape close to a cylinder. In addition, the shape has a value of a ratio of a thickness to a diameter (H/D in FIG. 2A) close to 1 (0.7 to 1.3).

First, regarding the weight of the crosshead 124, the vibration of the measurement unit 130 cannot be fully blocked if the weight is too low. On the other hand, the resonance frequency cannot be raised if the weight is too high. Accordingly, a certain level of the weight is required. Meanwhile, regarding the shape, the vibration has several modes including longitudinal vibration, bending vibration, swing vibration, and the like, and a probability of the occurrence of resonance along with any of the vibration modes becomes higher in a case where any of the thickness and the diameter is increased. It is therefore possible to raise an average resonance frequency by setting the ratio of the thickness to the diameter to a value close to 1.

As a result of the measurement, the resonance frequency of the crosshead 124 was successfully set around 4 kHz by adopting the above-described shape. Meanwhile, by using the above-described crosshead 124 in the dynamic characteristic measurement device 100, it is possible to measure the high-frequency range up to 3 kHz while eliminating an influence of the resonance frequency of the crosshead 124.

The measurement unit 130 includes the object 131 under test, the electrodynamic vibrator vibrating table 132, load washers 133, an accelerometer 134, distortion meters 135, a resonant jig 136, a position sensor 137, and a load washer attachment block 138.

In the case of the dynamic characteristic measurement device 100 of the present invention, the object 131 under test is a rubber isolator for an automobile and the like. Here, the rubber isolator includes a rubber isolator provided with a phase element such as a rubber isolator provided with a mass and a rubber isolator sealing a liquid. The object 131 under test is measured by being sandwiched between the electrodynamic vibrator vibrating table 132 and the load washers 133.

The electrodynamic vibrator vibrating table 132 is installed above the electrodynamic vibrator 113 and is controlled by the control system 200 to be described later. Although illustration is omitted, a vibrating plate 132a and a coil portion 132a are directly coupled to the electrodynamic vibrator vibrating table 132, and a direct-current magnetic field is arranged around them. The electrodynamic vibrator vibrating table 132 is driven by applying an electric current to this coil. Here, the vibration frequency range of the electrodynamic vibrator 113 is up to 3 kHz. However, the range is not particularly limited to 3 kHz and may be equal to or above 3 kHz.

The load washers 133 are attached via the load washer attachment block 138 to the crosshead 124 on the opposite side of the electrodynamic vibrator 113 for the object 131 under test. Each load washer 133 is a highly rigid piezoelectric element which has a high response speed and a small measurement threshold. Accordingly, the load washer 133 herein constitutes a dynamic load measuring instrument to measure a dynamic load applied to the object 131 under test. Note that four load washers 133 are arranged and installed as illustrated in FIG. 2B and an average value thereof is obtained. However, the present invention is not limited to this configuration.

As illustrated in FIG. 2B, the accelerometer 134 is attached to flanges on a side of the load washers 133 to which the object 131 under test is attached. The accelerometer 134 is provided in order to calculate a dynamic load from a measured acceleration rate in a case where the crosshead 124 vibrates, and to accurately measure the object 131 under test while eliminating an influence of the vibration. Accordingly, the measurement by using the accelerometer 134 does not have to be carried out in a case where the influence of the vibration of the crosshead 124 to the measurement accuracy is negligible.

The resonant jig 136 which also serves as a static load measurement unit is attached to a side of the electrodynamic vibrator vibrating table 132 near the object 131 under test. Here, the resonant jig 136 also serving as the static load measurement unit will be described by using FIGS. 4 to 5C.

Figure 4:
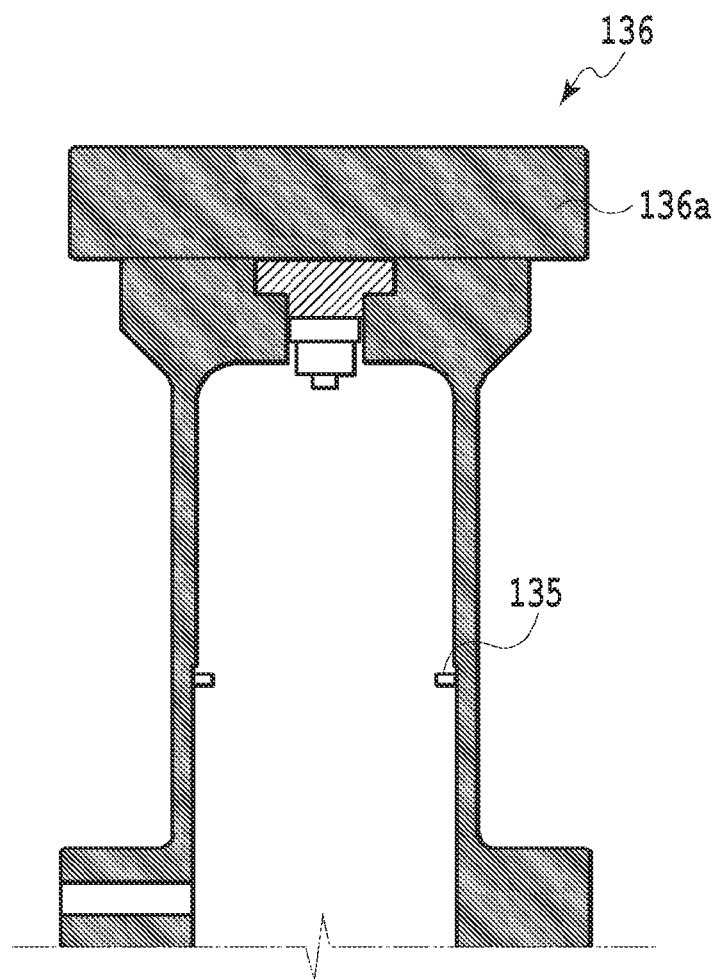
FIG. 4 is a cross-sectional view illustrating a resonant jig that also serves as a static load measurement unit of the dynamic characteristic measurement device shown in FIGS. 1 to 3.
Figure 5:
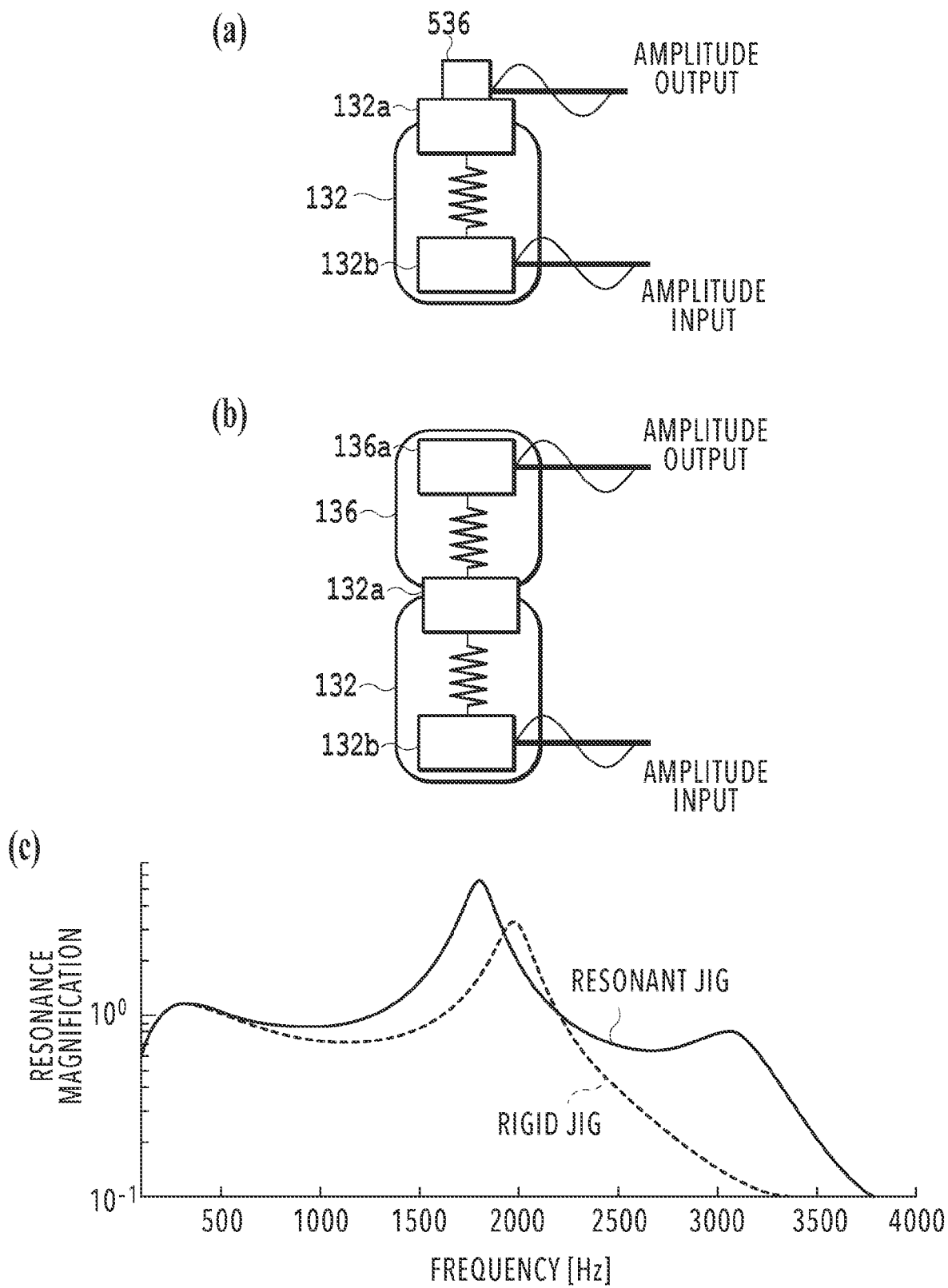
FIG. 5A is a schematic diagram illustrating a state of attaching a rigid jig to a conventional electrodynamic vibrator vibrating table.
FIG. 5B is a schematic diagram illustrating a state of attaching the resonant jig to the electrodynamic vibrator vibrating table.
FIG. 5C is a diagram illustrating a comparison between frequency characteristics in the states of attaching any of the rigid jig and the resonant jig.

FIG. 4 is a cross-sectional view illustrating the resonant jig 136 also serving as the static load measurement unit of the dynamic characteristic measurement device 100 shown in FIGS. 1 to 3. FIG. 5A is a schematic diagram illustrating a state of attaching a rigid jig 536 to a conventional electrodynamic vibrator vibrating table 132. FIG. 5B is a schematic diagram illustrating a state of attaching the resonant jig 136 to the electrodynamic vibrator vibrating table 132. FIG. 5C is a diagram illustrating a comparison between frequency characteristics in the states of attaching any of the rigid jig 536 and the resonant jig 136.

As illustrated in FIG. 4, the distortion meters 135 constituting the static load measurement unit are arranged at equal intervals on an inner periphery of the resonant jig 136 having a cylindrical shape here, and are capable of measuring a load in an axial direction. Note that a rigid block 136a for attaching the object 131 under test is provided above the resonant jig 136. The distortion meters 135 are provided for the purpose of measuring a static preload and are not affected by a dynamic load from an acceleration rate attributed to a mass of the block 136a and the like in an averaging procedure and a filtering procedure. In the meantime, the distortion meters 135 do not always have to be highly responsive. This static load measurement jig also has functions as the resonant jig as described below. However, the present invention is not limited to this configuration.

In the case of the rubber isolator for an automobile and the like, it is necessary to measure the dynamic characteristics in a state of application of a high load (a preload) on the assumption of a state of an actual vehicle. However, in the state of applying the preload as mentioned above, it is necessary to broaden a measurement range in a measurement of a dynamic load. In the case of the high frequency, a displacement of the object under test is reduced and the load is reduced as well. Accordingly, there is a problem a difficulty in measuring the load. Moreover, a performance of the rubber isolator does not have linearly and is therefore difficult to predict. Given the situation, the present invention newly provides the distortion meters 135 each serving as a static load measuring instrument, and is configured to improve an S/N ratio and to measure the dynamic load accurately by measuring only the dynamic load with the load washers 133 and reducing a measurement range of a charge amplifier 212 in a block diagram illustrated in FIG. 6.

As illustrated in FIG. 4, the resonant jig 136 is the cylindrical component attached to the electrodynamic vibrator vibrating table 132. It is possible to provide the resonant jig 136 with a desired resonance frequency by forming the resonant jig 136 into the cylindrical shape. As illustrated in FIG. 5A, the electrodynamic vibrator vibrating table 132 of the related art has a resonance point between the vibrating plate 132a and the coil portion 132a, and its vibration capacity is reduced in proportion to the square of the frequency after exceeding the resonance point. In addition, in the case where the rigid jig 536 is attached, the resonance point further drops and it is not possible to obtain a required vibration amplitude due to a drop in vibration capacity as illustrated in FIG. 5C. One conceivable method for reducing the aforementioned influence by the resonance is to raise the resonance point of the electrodynamic vibrator vibrating table 132. However, it is difficult to significantly change the resonance point from structural perspectives because its magnitude is almost determined by required vibration force and strokes. Another conceivable method is to increase the vibration force which may fulfill the required vibration force even in the case where the vibration capacity is reduced. However, this case will lead to increases in overall dimensions and costs of the device.

In contrast, in the case of attaching the resonant jig 136 to the electrodynamic vibrator vibrating table 132 as illustrated in FIG. 5B, it is possible to provide the resonant jig 136 with a desired resonance frequency, and thus to improve an amplitude level in a frequency band where the vibration capacity is reduced due to the resonance point of the electrodynamic vibrator vibrating table 132 as illustrated in FIG. 5C. Note that the amplitude level around 3 kHz being a measurement frequency band of the dynamic characteristic measurement device 100 of the present invention is improved herein. However, the present invention is not limited to this configuration. Meanwhile, in FIGS. 5A and 5B, it is also possible to consider that the electrodynamic vibrator vibrating table 132 is formed from the vibrating plate 132a and the coil portion 132a. In this case, it is possible to consider that a two-degrees-of-freedom resonance system is formed in conjunction with the cylindrical resonant jig 136. The amplitude level can be improved in the desired frequency band in this case as well.

Back to FIGS. 1 to 3, the position sensor 137 provided to the measurement unit 130 will be described.

The position sensor 137 is attached to the electrodynamic vibrator vibrating table 132 to measure a position of this electrodynamic vibrator vibrating table 132. Now, a description will be given of the electrodynamic vibrator vibrating table 132 and the position sensor 137 by using FIGS. 7A and 7B.

FIG. 7A is a block diagram illustrating open loop control of a conventional electrodynamic vibrator vibrating table 732 and FIG. 7B is a block diagram illustrating closed loop feedback control of the electrodynamic vibrator vibrating table 132.

In FIG. 7A, an instruction value to be inputted to the conventional electrodynamic vibrator vibrating table 732 configured to perform the open loop control is the acceleration rate. While the electrodynamic vibrator vibrating table 732 is driven by amplifying this acceleration rate, an output value therefrom is the acceleration rate again. In this case, since the acceleration rate is used as a signal value, this configuration is not suitable for feedback control to be described later and it is not possible to control an accurate position of the electrodynamic vibrator vibrating table 732.

In contrast, according to the dynamic characteristic measurement device 100 of the present invention, the position of the electrodynamic vibrator vibrating table 132 is measured by using the position sensor 137 and this displacement signal is used as a signal value as illustrated in FIG. 7B. In this way, a PID control unit can perform the feedback control of the electrodynamic vibrator vibrating table 132 by using a closed loop, thereby controlling an accurate position of the electrodynamic vibrator vibrating table 132. This position control function makes it possible to measure the static spring constant of the object under test.

Figure 6:
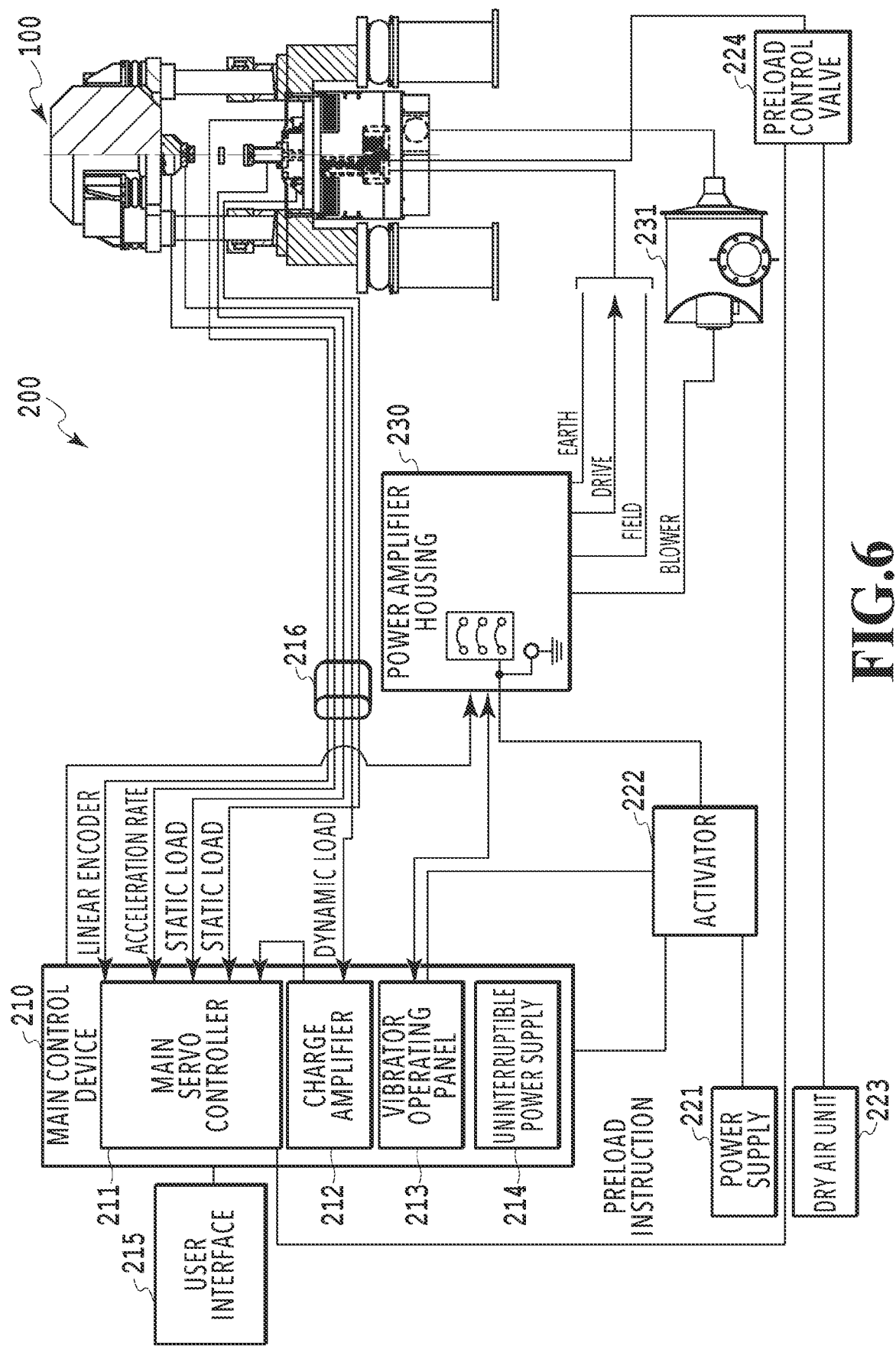
FIG. 6 is a system block diagram of a control system applied to the dynamic characteristic measurement device shown in FIGS. 1 to 3.

FIG. 6 is a system block diagram of the control system 200 applied to the dynamic characteristic measurement device 100 illustrated in FIGS. 1 to 3.

In FIG. 6, the control system 200 mainly includes a main control device 210, a power amplifier housing 230, and the like.

The main control device 210 is connected to a power supply 221 via an activator 222, connected to the dynamic characteristic measurement device 100 via an operating line 216, and configured to control the dynamic characteristic measurement device 100.

The main control device 210 mainly includes a main servo controller 211, the charge amplifier 212, a vibrator operating panel 213, an uninterruptible power supply 214, a user interface 215, and the like. Signals of the dynamic load, the static load, the displacement, the acceleration rate are inputted from various sensors of the dynamic characteristic measurement device 100 and various measurements and calculations are carried out. As described above, the main servo controller 211 can separately measure the dynamic load and the static load, and automatically change a measurement range and a display range depending on measured load levels.

The power amplifier housing 230 is controlled by a signal from the vibrator operating panel 213 of the main control device 210, and is configured to control operations of the electrodynamic vibrator vibrating table 132 of the electrodynamic vibrator 113 of the dynamic characteristic measurement device 100, for example.

As illustrated in FIG. 6, the control system 200 further includes a dry air unit 223 for applying the preload to the object 131 under test, a preload control valve 224 that controls a pressure from the dry air unit 223, a blower 231 for cooling the electrodynamic vibrator 113, and the like.

As described above, according to the dynamic characteristic measurement device of the present invention, it is possible to provide a dynamic characteristic measurement device which is capable of measuring a small dynamic load in a state of applying a preload while eliminating an influence of a resonance frequency of a frame even in a high-frequency vibration range up to 3 kHz, and of accurately measuring dynamic vibration characteristics of a rubber isolator and the like in the high-frequency vibration range by increasing a level of vibration of an object under test.

REFERENCE SIGNS LIST

100 dynamic characteristic measurement device
110 base
111 leg part
112, 122 air spring
113 electrodynamic vibrator
114 base mount part
120 support part
121 support pillar
123 fastener
124 crosshead
125 intermediate plate
130 measurement unit
131 object under test
132 electrodynamic vibrator vibrating table
133 load washer
134 accelerometer
135 distortion meter
136 resonant jig
137 position sensor
138 load washer attachment block
200 control system
210 main control device
211 main servo controller
212 charge amplifier
213 vibrator operating panel
214 uninterruptible power supply
215 user interface
216 operating line
221 power supply
222 activator
223 dry air unit
224 preload control valve
230 power amplifier housing
231 blower

The invention claimed is:

1. A dynamic characteristic measurement device comprising:
   a base;
   a support part placed above the base so as to be capable of floating via an elastic body;
   an electrodynamic vibrator provided on the base side of an object under test mounted between the base and the support part and configured to vibrate the object under test; and
   a dynamic load measuring instrument provided on the support part side of the object under test and configured to measure a dynamic load applied to the object under test, wherein
   the shape of support part is such that a resonant frequency of the support part is at least 3 kHz, and
   the dynamic characteristic measurement device further includes a static load measuring instrument attached to the electrodynamic vibrator and configured to measure a static load applied to the object under test.

2. The dynamic characteristic measurement device according to claim 1, wherein the static load measuring instrument is attached to a resonant jig attached to the electrodynamic vibrator.

3. The dynamic characteristic measurement device according to claim 1, wherein an accelerometer configured to remove an influence of the dynamic load to the support part is attached to the dynamic load measuring instrument.

4. The dynamic characteristic measurement device according to claim 1, wherein
   a position sensor configured to measure a position of the electrodynamic vibrator is attached to the electrodynamic vibrator, and
   vibration of the electrodynamic vibrator is controlled by feedback control based on a displacement signal from the position sensor.

5. The dynamic characteristic measurement device according to any one of claims 1 to 4, wherein a preload is applied from the electrodynamic vibrator side to the object under test.

6. The dynamic characteristic measurement device according to claim 1, wherein the static load measuring instrument is configured to measure a preload applied to the object under test.

7. The dynamic characteristic measurement device according claim 6, wherein the static load measuring instrument comprises a strain gauge to measure the preload applied to the object under test.

8. The dynamic characteristic measurement device according claim 1, wherein the support part comprises a crosshead, a ratio of a height to a diameter of the crosshead being between 0.7 to 1.3.

* * * * *